(12) United States Patent
Oelz et al.

(10) Patent No.: US 10,940,091 B2
(45) Date of Patent: Mar. 9, 2021

(54) ORAL MEDICINE DISPENSING SYSTEM

(71) Applicants: Alexander Markus Oelz, Constantia (ZA); Robert James Martin, Constantia (ZA)

(72) Inventors: Alexander Markus Oelz, Constantia (ZA); Robert James Martin, Constantia (ZA)

(*) Notice: Subject to any disclaimer, the term of this patent is extended or adjusted under 35 U.S.C. 154(b) by 377 days.

(21) Appl. No.: 15/977,533

(22) Filed: May 11, 2018

(65) Prior Publication Data

US 2018/0344574 A1 Dec. 6, 2018

Related U.S. Application Data

(63) Continuation-in-part of application No. 14/406,200, filed as application No. PCT/IB2013/054852 on Jun. 13, 2013, now Pat. No. 9,974,712.

(30) Foreign Application Priority Data

Jun. 15, 2012 (GB) .................................. 1210628.2

(51) Int. Cl.
*A61J 7/00* (2006.01)
*A61M 5/31* (2006.01)
(Continued)

(52) U.S. Cl.
CPC .............. *A61J 7/0053* (2013.01); *A61M 5/19* (2013.01); *A61M 5/2448* (2013.01);
(Continued)

(58) Field of Classification Search
CPC .......... A61M 39/221; A61M 2039/222; A61M 39/18; A61M 5/3134; A61J 7/0053
See application file for complete search history.

(56) References Cited

U.S. PATENT DOCUMENTS 1,231,497 A 6/1917 Cook
1,943,120 A 1/1934 Kabnick
(Continued)

FOREIGN PATENT DOCUMENTS

AT 12002 9/2011
CN 2518508 10/2002
(Continued)

OTHER PUBLICATIONS

World Intellectual Property Organization, International Search Report and Written Opinion, dated Dec. 20, 2013, issued in International Patent Application No. PCT/IB2013/054852.
(Continued)

*Primary Examiner* — Nathan R Price
*Assistant Examiner* — Courtney B Fredrickson
(74) *Attorney, Agent, or Firm* — Klarquist Sparkman, LLP

(57) ABSTRACT

A liquid dispensing system for oral administration comprises a dispenser (16,18,20) and cartridges (14) from which medicine is dispensed. Each cartridge (14) includes a hollow shell (22,24) with a septum (26) at one end, a piston (28) at the other end, and the medicine in a cavity (23) between the septum and the piston. The dispenser includes receiver (20) in which a cartridge (14) is received, a plunger (18) that can slide relative to the receiver and that has a plunging head (52) that can drive the piston (28), and a barrel (16) in which the cartridge (14), receiver (20) and plunger (18) can be received, at least partly. Once a cartridge (14) has been inserted into the receiver (20), the receiver and cartridge are inserted into the barrel (16) and a piercing head (44) ruptures the septum (26). The plunger (18) is pushed to drive the piston (28) and the medicine is dispensed by the piston, through a discharge passage (42) of the barrel (16). The septum (26) can hinge on a hinge formation (86) to act as a
(Continued)

one-way valve to prevent unintentional flow of liquid from the cartridge.

19 Claims, 7 Drawing Sheets

(51) Int. Cl.
  *A61M 5/315* (2006.01)
  *A61M 5/24* (2006.01)
  *A61M 5/19* (2006.01)

(52) U.S. Cl.
  CPC ........ *A61M 5/2466* (2013.01); *A61M 5/3129* (2013.01); *A61M 5/3134* (2013.01); *A61M 5/31505* (2013.01); *A61M 5/31525* (2013.01); *A61M 5/31578* (2013.01); *A61M 2005/31506* (2013.01); *A61M 2005/31516* (2013.01)

(56) References Cited

U.S. PATENT DOCUMENTS

| | | | |
|---|---|---|---|
| 2,531,893 A | 11/1950 | Roehr | |
| 4,445,895 A | 5/1984 | Margulies | |
| 5,468,232 A * | 11/1995 | Naganuma | A61M 5/24 604/200 |
| 6,123,688 A | 9/2000 | Botich et al. | |
| 6,221,055 B1 | 4/2001 | Shaw et al. | |
| 6,386,872 B1 * | 5/2002 | Mukasa | A61C 5/64 206/219 |
| 2005/0154354 A1 | 7/2005 | Kawasaki et al. | |
| 2008/0097338 A1 | 4/2008 | Cheng et al. | |
| 2010/0280453 A1 | 11/2010 | Li | |

FOREIGN PATENT DOCUMENTS

| | | |
|---|---|---|
| EP | 1 927 372 A1 | 6/2008 |
| WO | WO 2010/022870 | 3/2010 |
| WO | WO 2012/059455 | 5/2012 |

OTHER PUBLICATIONS

State Intellectual Property Office of the People's Republic of China, First Office Action, dated Jun. 27, 2016, issued in China Patent Application No. 2013800312488.

* cited by examiner

ORAL MEDICINE DISPENSING SYSTEM

CROSS-REFERENCE TO RELATED APPLICATIONS

This is a continuation-in-part of application Ser. No. 14/406,200, filed Dec. 5, 2014, now U.S. Pat. No. 9,974,712, which was the National Stage of International Application No. PCT/IB2013/054852, filed Jun. 13, 2013, which claims priority to United Kingdom Patent Application No. 1210628.2, filed Jun. 15, 2012. All of these applications are hereby incorporated herein by reference in their entireties.

FIELD

This invention relates to dispensing system that is suitable for supply and oral administration of medicines, particularly to infants and small children (who are collectively referred to as "children" herein).

BACKGROUND

Medicines can be harmful if ingested accidentally and while adults usually know to avoid doing so, children are at risk and there is a need to prevent accidental ingestion of medicines.

Further, liquid medicines need to be administered in measured dosages, usually orally, and in order to allow measurement of the correct dosages and administration, the medicines are typically supplied in bottles with large enough openings to allow the medicine to be poured (e.g. in to a spoon) or withdrawn (e.g. with a syringe). These operations are cumbersome, are often performed in the presence of children and often by a person who is also tasked with controlling a child. As a result, there are significant risks of spillage (whether through handling error by the adult or by the child), inaccurate dosage measurement (because the adult is distracted or physically hindered), accidental ingestion (if the medicine container is not closed immediately), and unsuccessful or incomplete administration of the medicine. These risks are increased in instances where more than one child is present and/or where a child is restless—which is common in the cases of children who are unwell or who resist medication.

Many attempts have been made to prevent unwanted opening of the containers in which liquid medicines are supplied, but these do not address the problems mentioned above, which necessarily arise at the time that the adult has to open the container to administer medicine.

Attempts have been made to avoid the risks and inconvenience associated with measuring dosages of liquid medicines and to reduce the volume of liquid in packaging that could be ingested, by supplying liquid medicines in unit dosages in sachets and small plastic containers with twist-off caps, but the sachets and other containers do not provide for convenient administration of the medicine. It is also very difficult to administer a fraction of a dosage (e.g. a half dosage) from such a sachet or container.

Unit dosages of liquid medicines have also been supplied in glass vials with necks that need to be severed—creating dangerous edges around the necks of the vials and creating small glass fractures—both of which pose considerable risk of injury.

Many devices for dispensing medicines are made from multiple materials and/or from materials that are difficult to recycle or that cannot be recycled.

Devices intended to prevent accidental ingestion or to assist in administration of medicines are typically costly.

The present invention seeks to reduce the risk of accidental ingestion of liquids and to provide for dispensing of liquids that overcomes most or all of the shortfalls mentioned above.

SUMMARY

According to one aspect of the present invention there is provided a system for dispensing liquid medicine for oral administration, said system comprising:
  at least one cartridge that includes;
    a hollow, elongate shell that has a longitudinal axis and that defines an internal cavity and that is closed at one end with a substantially rigid septum, at least a first part of the periphery of the septum being attached to the closed end of the shell by at least one rupture formation that is thinner than the septum and is thin enough to rupture when pierced with a sharp object, and at least a second part of the periphery of the septum being attached to the closed end of the shell by at least one hinge formation that is thinner than the septum and is thin enough to allow the septum to hinge relative to the shell, about the hinge formation;
    a piston that is disposed inside the shell and that can slide axially inside the cavity while sealing against the inside of the shell; and
    said liquid medicine being held inside the cavity between the closed end and the piston; and
  a dispenser that includes:
    a body defining a receiving formation in which at least the closed end of the shell of the cartridge is receivable;
    a sharp protuberance disposed in the receiving formation and configured to rupture the rupture formation if the cartridge is moved far enough in the axial direction; and
    a plunger that is displaceable in the axial direction towards the protuberance.

According to another aspect of the present invention there is provided a cartridge for dispensing liquid medicine for oral administration, said cartridge comprising:
  a hollow, elongate shell that has a longitudinal axis and that defines an internal cavity and that is closed at one end with a substantially rigid septum;
  a piston that is disposed inside the shell and that can slide axially inside the cavity, while sealing against the inside of shell;
  said liquid medicine being held inside the cavity between the closed end and the piston;
  wherein at least a first part of the periphery of the septum is attached to the closed end of the shell by at least one rupture formation that is thinner than the septum and is thin enough to rupture when pierced with a sharp object; and
  wherein at lease a second part of the periphery of the septum is attached to the closed end of the shell by at least one hinge formation that is thinner than the septum and is thin enough to allow the septum to hinge relative to the shell, about the hinge formation.

The term "substantially rigid" is used herein to refer to rigidity of the septum being substantially more than the rigidity of the adjacent rupture formations and hinge formations—even though the material of these formations are the same as the septum and the relative rigidity of the septum is achieved through its thickness.

The at least one rupture formation and the at least one hinge formation may extend contiguously around the periphery of the septum, in particular, they may extend continuously along the periphery of the septum to form a continuous thin-walled border along at least part of the periphery of the septum or the thin-walled border may extend continuously along the entire periphery of the septum.

The system may include at least one sealing lip that extends from the septum, on the side of the septum that faces towards the cavity, said sealing lip overlapping the rupture formation at least in part. The system may include a plurality of said sealing lips that extend contiguously along the periphery of the septum.

The dispenser may include a receiver defining a recess in which the cartridge is receivable, at least in part, said plunger being attachable to the receiver, to slide relative to the receiver and cartridge shell in the axial direction. The cartridge may be held in place in the recess of the receiver, by releasable lock formations.

The receiver may include a first detent that is biased towards a locked position in which it prevents sliding movement between the plunger and the receiver, said first detent being displaceable against its bias, by the body, when the receiver engages the body.

The receiver may include a second detent that is biased towards a locked position in which it prevents sliding movement between the plunger and the receiver, said second detent being displaceable against its bias, by the cartridge, when the cartridge is received inside the recess of the receiver.

The receiving formation of the body may be a cavity in which the receiver and cartridge are receivable to engage the receiver and body, and the sharp protuberance may be defined inside the cavity.

The body may define a stop formation adjacent the sharp protuberance to inhibit the receiver and cartridge from sliding in the axial direction to a point at which the sharp protuberance can rupture the septum, unless the receiver and cartridge are inserted into the body with a correct orientation. A corresponding recess may be defined in the receiver, which can receive the stop formation with interference, so that the receiver and cartridge can slide in the axial direction against said interference, while the sharp protuberance ruptures the septum.

The piston may have a leading side, which faces towards the closed end of the cartridge shell and a recess may be defined in the leading side of the piston, which is shaped and dimensioned to receive an end of the sharp protuberance when the septum has been ruptured. The piston may be welded to the shell, said weld being small enough to be ruptured when the plunger pushes the piston in the axial direction.

The shell, piston and dispenser may be made from recyclable plastics materials.

BRIEF DESCRIPTION OF THE DRAWINGS

For a better understanding of the present invention, and to show how the same may be carried into effect, the invention will now be described by way of non-limiting example, with reference to the accompanying drawings in which.

DETAILED DESCRIPTION

Figure 1:
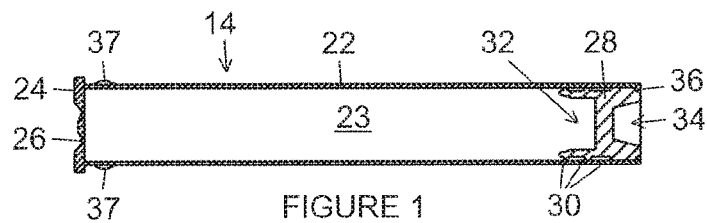
FIG. 1 shows a sectional side view of a cartridge according to a first embodiment of the present invention.
Figure 2:
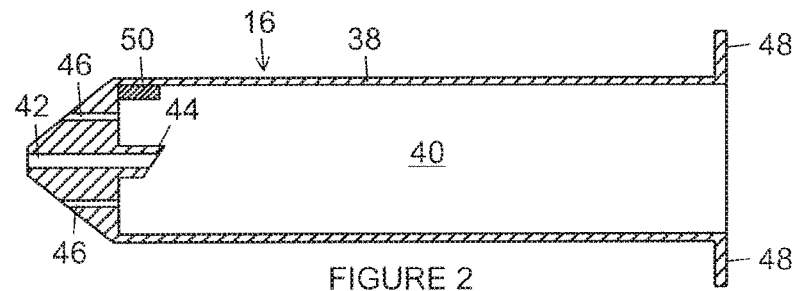
FIG. 2 shows a sectional side view of a dispenser body according to the first embodiment of the present invention.

Referring to FIGS. 1 to 10 of the drawings, a system according to a first embodiment of the present invention for dispensing liquid medicine for oral administration, includes a cartridge 14, a body in the form of a barrel 16, a plunger 18 and a receiver 20.

The cartridge 14 has a shell that comprises of a hollow cylinder 22 with an internal cavity 23 and a disc 24 that forms a closed end of the shell. The disc 24 forms a central septum 26, at least part of which is thinner than the remainder of the disc, so that the septum can rupture when pierced with a sharp object. The cylinder 22, disc 24 and septum 26 are injection moulded as a unitary moulding from a recyclable plastics material. The cartridge shell has a longitudinal axis (that is not shown in the drawings), which forms a common axis for the barrel 16, plunger 18 and receiver 20.

A piston 28 is disposed inside the cylinder 22 and can slide axially inside the cylinder with the circumference of the piston sealing against the inner circumference of the cylinder. The piston 28 is also injection moulded from recyclable plastics material and it has circumferential ridges 30 that slide along the inside of the cylinder 22 with light interference, to provide the necessary seal. The piston 28 is shown in FIG. 1 at the start of its stroke, in which it travels in an axial direction (to the left in FIG. 1) from the open end of the cylinder 22 towards its closed end. The part of the cavity 23 between the piston 28 and the disc 24 is filled with a liquid medicine.

On a leading side of the piston 28, it defines a leading recess 32 for receiving an end of a sharp protuberance (see below) that ruptures the septum 26, as well as the ruptured part of the septum, when the piston is at the end of its stroke. The leading recess 32 allows the piston 28 to continue with its stroke up to a point where the piston buts against the disc 24, so that the only part of the cavity 23 that remains between the piston 28 and the disc 24 is the inside of the leading recess 32. The leading recess 32 thus assists in purging medicine from the cavity 23 and minimises medicine waste. It also increases dispensing accuracy, and reduces the necessary piston stroke length for optimum cartridge length—i.e. the cartridge does not need to be longer, to provide sufficient internal space for the full piston stroke.

On a trailing side of the piston 28, it defines a trailing recess 34, in which the plunging head of the plunger (see below) is receivable to drive the piston during its stroke.

At its open end, the cylinder 22 has a small inner retaining ridge 36, which prevents the piston 28 from exiting the cylinder. In addition, when the cartridge 14 is supplied, i.e. in the condition shown in FIG. 1, before the piston 28 begins its stroke, its circumference at its trailing side is preferably welded to the retaining ridge 36, to ensure that the piston does not dislodge prematurely from its position in the cylinder and to ensure that the cavity 23 is perfectly sealed. The weld is very small and is severed easily when the piston 28 is driven during its stroke, but assists the retaining ridge 36 in preventing accidental dislodgement of the piston and spillage, e.g. if the cartridge 14 is bent or compressed.

On the outside of the cylinder 22, near the disc 24, lock formations are provided in the form of small rounded protuberances 37.

The recyclable plastics materials from which the cartridge 14 (apart from the medicine) is made, are selected such that the cylinder 22 can be mechanically flattened or completely bent, without breaking. The cylinder 22 also has very thin walls and can be produced at very low cost. The fact that the entire cartridge 14 is made from recyclable materials (apart from the medicine), allows the cartridge to be recycled easily, once the medicine has been dispensed, without a need to separate components of the cartridge. The cartridge 14 is intended to be a disposable item.

The barrel 16 is a unitary moulding that has an elongate shape with a peripheral wall 38 around a receiving formation in the form of an internal recess 40. The barrel 16 defines a central discharge passage 42 at a closed end of the recess, with a sharp protuberance in the form of a hollow piercing head 44 extending around the discharge passage and protruding into the recess 40. The piercing head 44 is sharp and hard enough to rupture the septum 26 of the cartridge 14, if the cartridge is inserted deep enough into the recess 40, with a moderate force. Two drainage passages 46 are defined adjacent the discharge passage 42, to allow easy rinsing and drainage of the recess 40, when washed. Two tabs 48 extend from opposing sides of the recess 40's opening and a stop formation in the form of a key 50 is provided inside the recess.

The plunger 18 is a unitary moulding that includes an elongate plunging head 52, with one or more generally parallel guides 54 on opposing sides of the plunging head, the plunging head and guides being joined by a plunger disc 56. The ends of the guides 54 that are opposite from the disc 56 are wider, to form steps 58

The receiver 20 defines a recess 60 inside which the cartridge 14 is snugly receivable. Near an open end of the recess 60, a locking formation in the form of a rounded circumferential groove 62 is defined on the inside of the recess, in which the protuberances 37 of the cartridge 14 are receivable in a clicking fashion, to hold the cartridge releasably in place inside the recess. At a closed end of the recess 60, a central plunge passage 64 is defined, extending axially from the recess, with a shoulder 66 extending around the plunge passage. The retaining ridge 36 rests against the shoulder 66 when the cartridge 14 is received inside the recess 60, The receiver 20 defines guide passages 68 in which the guides 54 can slide and tabs 70 extend on opposing sides of the receiver and partially obstruct the openings of the guide passages, with shoulder formations 72. In a peripheral wall of the receiver 20, near one of the tabs 70, a first detent 74 is defined, which is biased to protrude outwards from the peripheral wall. The receiver 20 defines a recess (not shown) in which the key 50 is receivable, with light interference.

Figure 6:
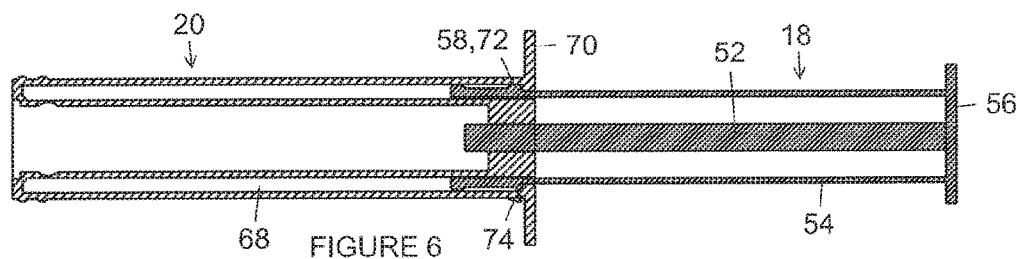
FIG. 6 shows the receiver of FIG. 5 in combination with the plunger of FIG. 4.

Referring to FIG. 6, the receiver 20 and plunger 18 are preferably pre-assembled, with the guides 54 being received inside the guide passages 68 and being held captive within the guide passages by the steps 58 and shoulder formations 72, which prevent withdrawal of the guides from the guide passages.

The plunger 18 can slide easily relative to the receiver 20, but when the plunger is in a retracted position, as shown in FIG. 6, in which it is withdrawn to the point at which the shoulder formations 72 and steps 58 make contact, the detent 74 locks the plunger and receiver relative to each other, to prevent sliding between them. The lock can only be released if the receiver is slid into the recess 40 of the barrel—which will push the detent 74 inwards and release its lock.

Figure 7:
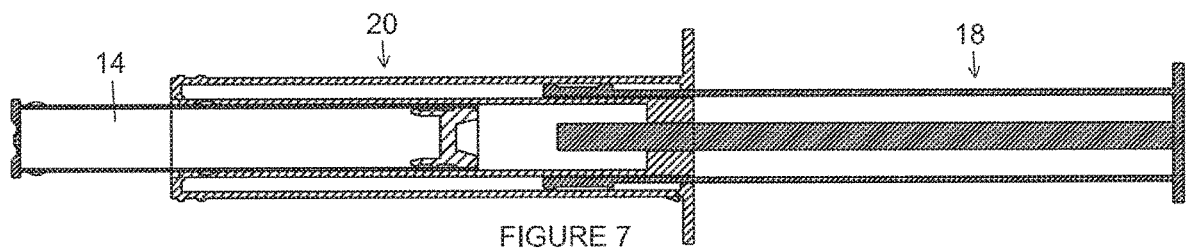
FIG. 7 shows the receiver/plunger combination of FIG. 6; with the cartridge of FIG. 1 partly inserted into the receiver.
Figure 8:
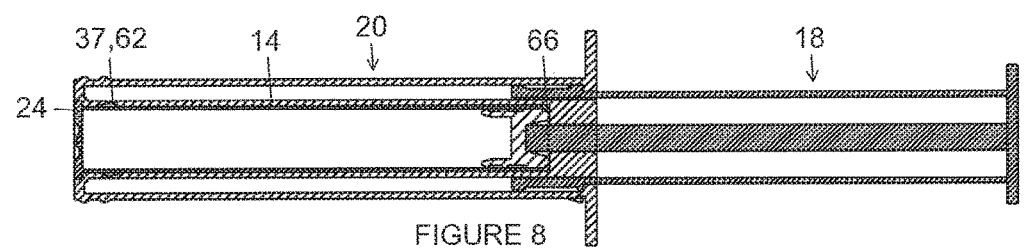
FIG. 8 shows the receiver/plunger combination and cartridge of FIG. 7 with the cartridge fully inserted into the receiver.

In use, when a liquid medicine is to be dispensed, e.g. to be administered orally to a patent, a cartridge 14 is selected that contains the required unit dosage of the required medicine and the cartridge is inserted into the recess 60 of the receiver 20 as shown in FIGS. 7 and 8, until the disc 24 is generally flush with the open end of the recess 60, the protuberances 37 are received in the groove 62, and the plunger is locked in its fully retracted position. The plunger 18 can either be in its fully retracted position before the cartridge 14 is inserted, or the cartridge will push the plunger to its fully retracted position.

Figure 3:
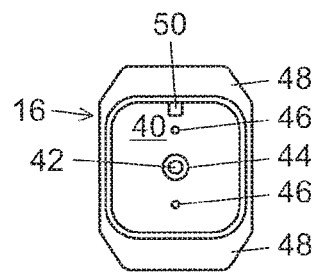
FIG. 3 shows an axial end view of the body of FIG. 2.
Figure 4:
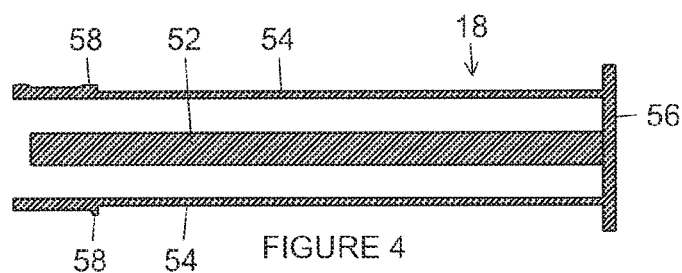
FIG. 4 shows a sectional side view of a plunger according to the first embodiment of the present invention.
Figure 5:
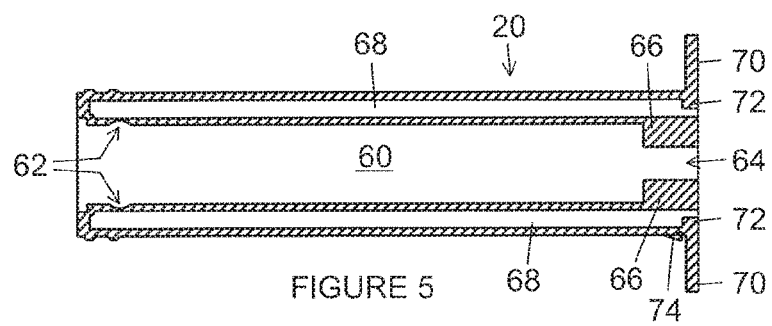
FIG. 5 shows a sectional side view of a receiver according to the first embodiment of the present invention.

Once the cartridge 14 has been loaded into the receiver 20, the receiver is inserted into the recess 40 of the barrel 16. As shown in FIG. 3, the barrel 16 is not cylindrical in cross sectional profile and in order to provide additional safety, the receiver 20 has to be inserted into the recess 40 with a correct orientation, for the key 50 to be received inside the corresponding recess on the receiver. If a child were to attempt to use the dispenser, there is a good chance that the receiver 20 will have the wrong orientation if it is inserted into the recess 40 and accordingly, the end of the receiver will but against the key 50 and the cartridge 14 will not make sufficient contact with the piercing head 44 to rupture the septum 26.

Figure 9:
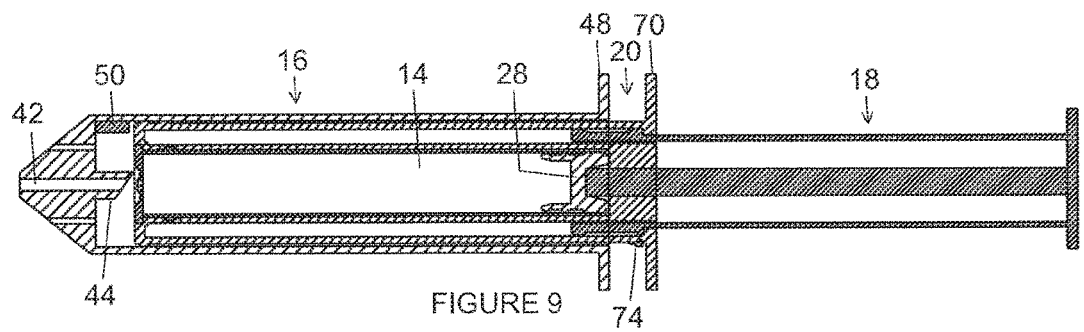
FIGS. 9, 9A and 9B show the receiver/plunger combination and cartridge of FIG. 8, with the receiver and cartridge inserted into the body of FIGS. 2 and 3, to form a system comprising a dispenser and cartridge that are ready for dispensing medicine.
Figure 9A:
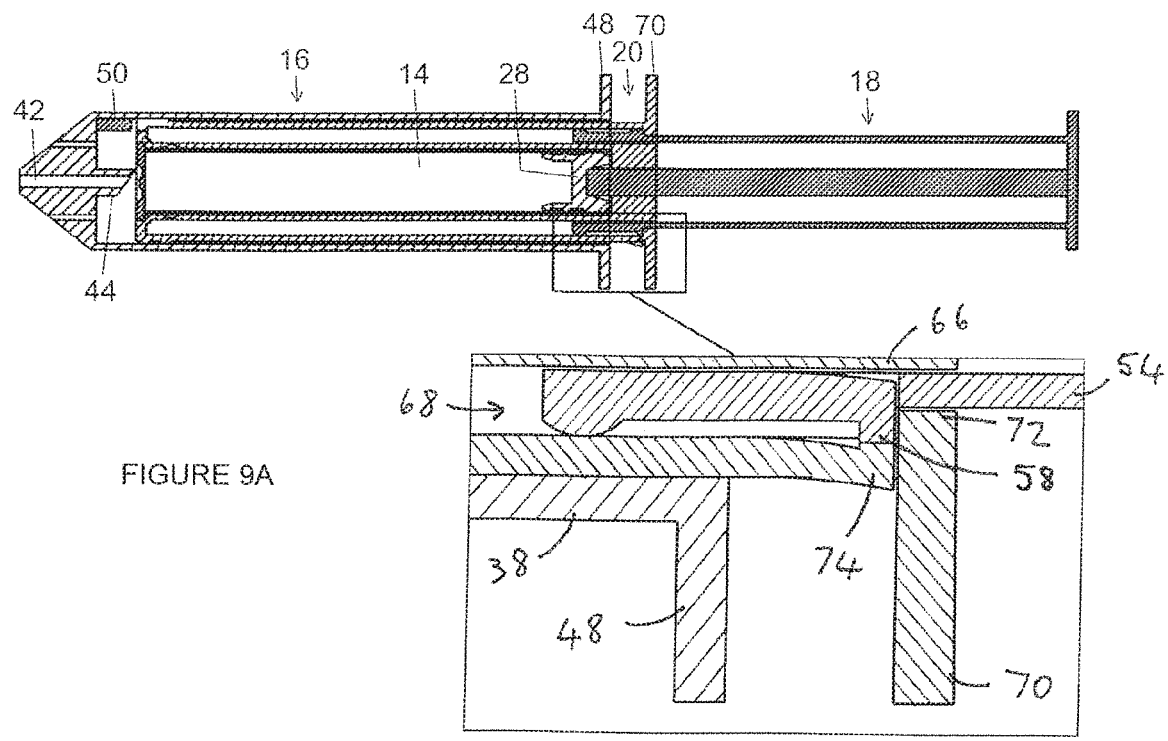
Figure 9B:
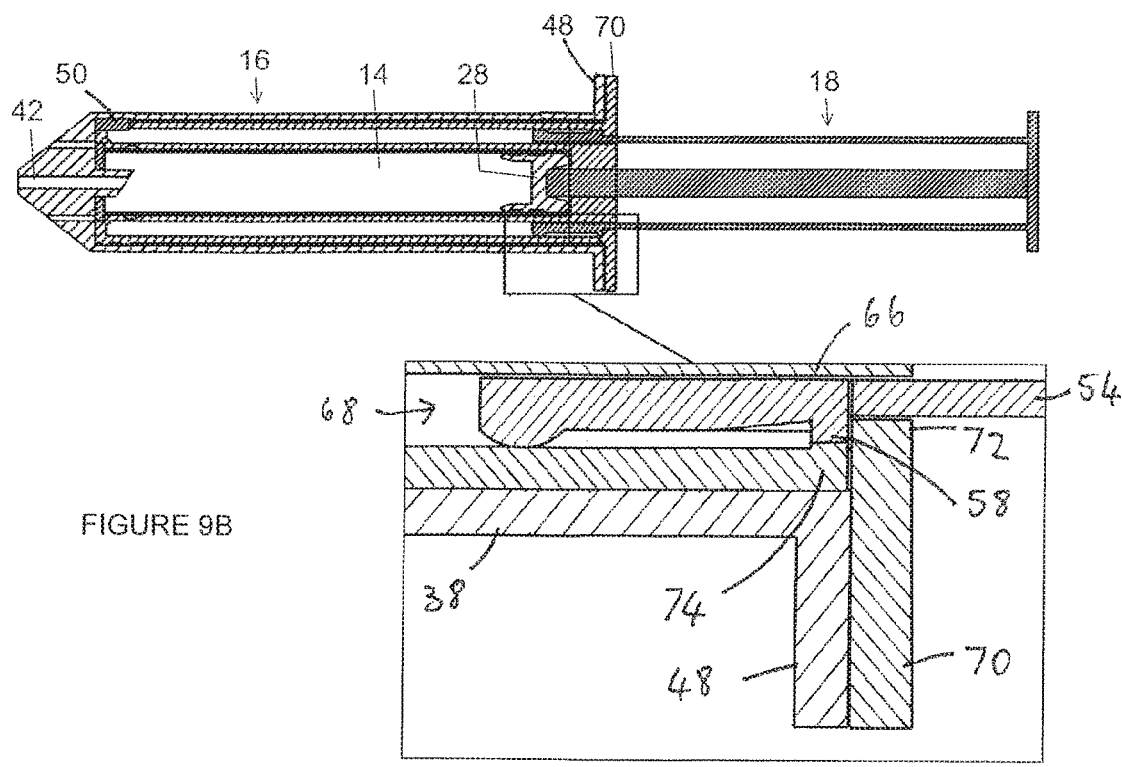

If the receiver 20 is inserted correctly into the recess 40 of the barrel 16, it will slide relatively easily up to the position shown in FIG. 9A and it will require a noticeable, yet moderate increase in force to urge the receiver and cartridge 14 deeper into the recess 40. As shown in FIG. 9B, as the receiver 20 and cartridge 14 slide right to the closed end of the recess 40, the piercing head 44 ruptures the septum 26, so that the cavity 23 inside the cartridge is in flow communication with the discharge passage 42. The increase in required effort reduces the likelihood that the receiver 20 and cartridge 14 will be fully inserted into the recess 40 and the septum 26 ruptured prematurely or inadvertently.

At the point where the receiver 20 and cartridge 14 have been inserted fully into the recess 40, the tabs 48,70 of the barrel 16 and receiver 20 are close together and the outer wall of the barrel urges the detent 74 inwards to push the step 58 inwards and release it from a recess adjacent the detent, to release the plunger 18 to slide relative to the receiver. The user gently pushes the plunger disc 56 towards the barrel 16, receiver 20 and cartridge and while doing so, the plunging head 52 urges the piston 28 along its stroke, as described above and the piston expels the medicine from the cavity, via the discharge passage 42. The closed end of the barrel 16 can be inserted into a patient's mouth for direct oral administration of the medicine, or the medicine can be dispensed in any other way, e.g. into a spoon.

The diameter of the cylinder 22, stroke of the piston 28, and length and diameter of the discharge passage 42 are designed to minimise the flow rate at which the liquid medicine is dispensed—which assists in minimising spillage when dispensing, e.g. into a spoon or cup, or orally. This is a significant improvement over the short length syringes with wide bodies that are often used for dispensing medicines and which have high liquid delivery flow rates.

Figure 10:
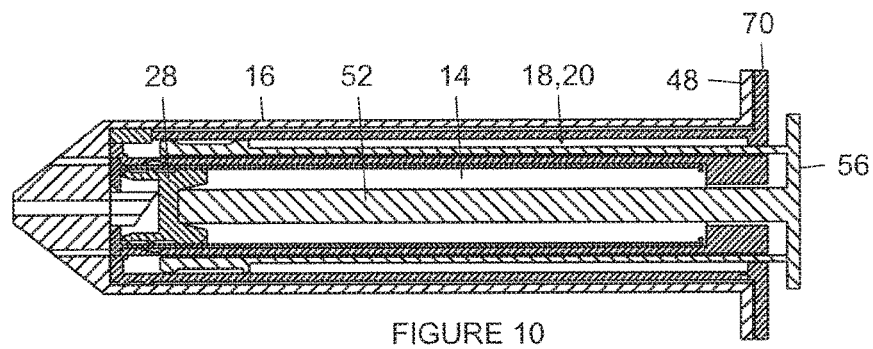
FIG. 10 shows the dispenser and cartridge of FIG. 9 after medicine has been dispensed.

Once the piston 28 has completed its stroke, the remaining volume of the cavity 23, and thus the remaining volume of medicine in the cartridge are very small and the apparatus are in the condition shown in FIG. 10. The receiver tabs 70 can now be pulled to withdraw the receiver 20 from the barrel 16 and once the receiver 20 has been completely withdrawn, the plunger disc 56 is pushed towards the receiver, to expel the spent cartridge 14 from the receiver.

Figure 11:
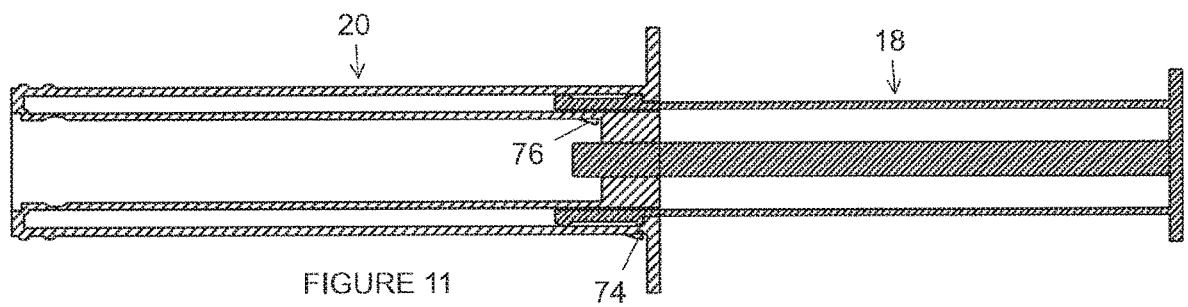
FIG. 11 shows an alternative embodiment of the receiver/plunger combination of FIG. 6, according to a second embodiment of the present invention.

Referring to FIG. 11, in a second embodiment of the invention, a second detent 76 may be provided in the inner wall of the receiver 20, which is biased to extend into the recess 60 and which locks the plunger 18 against sliding relative to the receiver 20. The detent 76 is configured to be displaced outwards against its bias by the open end of the cylinder 22 when the cartridge 14 is fully inserted into the recess 60, to release the detent's lock so that the plunger 18 can slide relative to the receiver 20.

Figure 12:
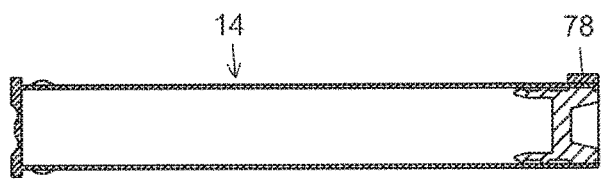
FIG. 12 shows an alternative embodiment of the cartridge of FIG. 1, according to a third embodiment of the present invention.

Referring to FIG. 12, in a third embodiment of the invention, a key may be provided on the outside of the cartridge 14, which is receivable in a corresponding slot (not shown) in the receiver 20. The key and slot can be configured to prevent an incorrect cartridge 14 (which will have a different key) from being inserted into the receiver 20. The keys 78 could be unique for different medicines, dosages, suppliers, or the like.

Figure 13:
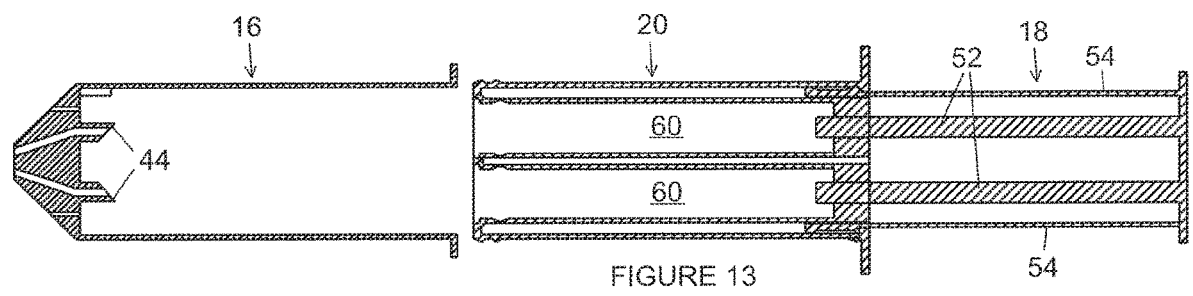
FIG. 13 shows an exploded sectional side view of a dispenser body and the combination of a receiver and plunger according to a fourth embodiment of the present invention.
Figure 14:
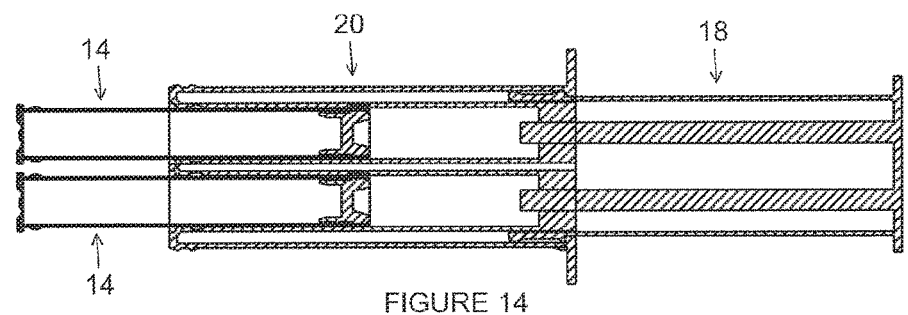
FIG. 14 shows the receiver/plunger combination of FIG. 13; with the two of the cartridges of FIG. 1 partly inserted into the receiver.
Figure 15:
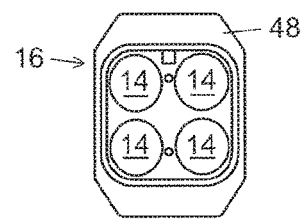
FIG. 15 shows an axial end view of the body of FIG. 13, and shows the positions of four cartridges.

Referring to FIGS. 13 to 15, a system for dispensing liquid medicine according to a fourth embodiment of the invention is similar to the system according to the first embodiment of the invention shown in FIGS. 1 to 10 and features that are similar between the two embodiments are identified by like reference numerals.

The barrel 16, plunger 18 and receiver 20 shown in FIGS. 13 to 15 are configured to dispense medicine simultaneously from four cartridges 14. The receiver 20 defines four recesses 60 in which the cartridges 14 are received in the same way as in the first embodiment of the invention and the plunger 18 has four plunging heads 52 that expel medicine from the cartridges, with guides 54 on the outsides of the plunging heads. The barrel 16 is shaped to receive the larger receiver 20 and has four piercing heads 44 positioned to rupture the septums of the four cartridges.

The system shown in FIGS. 13 to 15 holds the advantage that a larger dosage of medicine can be dispensed in a single action, but if a smaller dosage is required, fewer cartridges 14 can be inserted into the receiver 20. It is similarly envisaged that a medicine dispensing system according to the invention can be made for any other number of cartridges.

Figure 16:
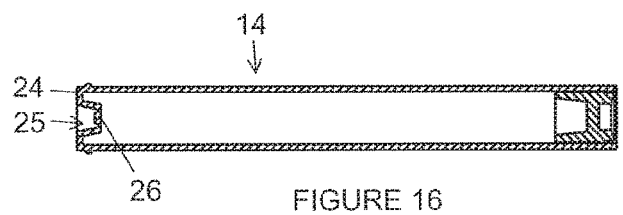
FIG. 16 shows a sectional side view of a cartridge according to a fifth embodiment of the present invention.
Figure 17:
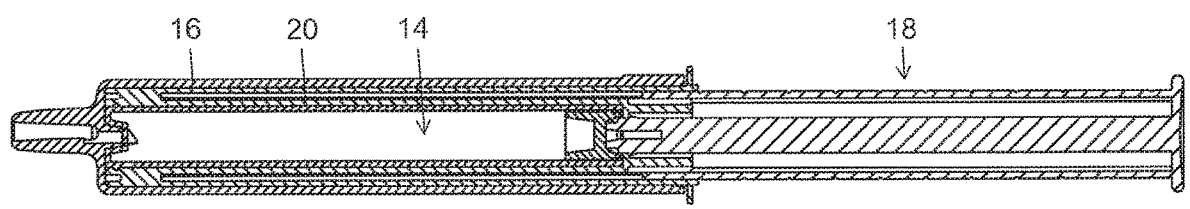
FIG. 17 shows the dispenser of FIG. 16 in use in a dispenser according to the fifth embodiment of the invention.

Referring to FIGS. 16 and 17, in a fifth embodiment of the present invention, a single cartridge 14 and dispenser (comprising a barrel 16, plunger 18 and receiver 20) are provided that are functionally similar to those shown in FIGS. 1 to 10 and like features are therefore identified by the same reference numerals as used in FIGS. 1 to 10. The term "disc" is used for a formation in FIGS. 16 and 17 that is not strictly disc shaped, but it performs the same function as the disc shown in FIGS. 1 to 10.

In the fifth embodiment, the disc 24 and septum 26 are configured such that the septum is at the back of a recess 25 in the front end of the cartridge 14, to reduce the likelihood that the septum would be pierced by any other sharp object, such as a pen. Further, the scored part of the disc 24 that forms the circumference of the septum 26, where the disc can rupture, is disposed in the corner of the recess 25 and accordingly, an object inserted into the recess is only likely to rupture the disc if it reaches into the corner. If such an object presses against the septum 26 away from the corner, the stress caused would be distributed across the disc 24 and the likelihood that the septum would rupture is small.

Figure 18:
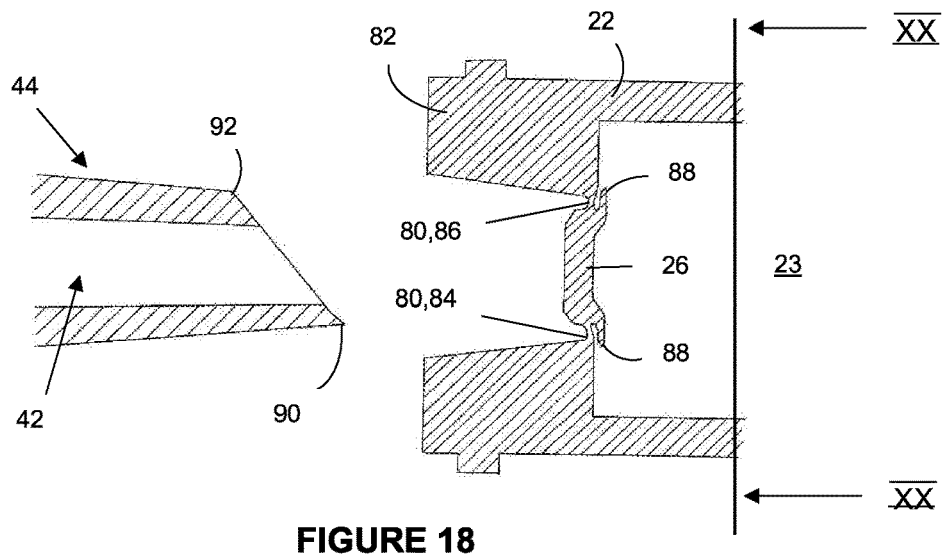
FIG. 18 shows a detail, exploded, cross-sectional view of a piercing head and end of a cartridge according to a sixth embodiment of the present invention, prior to use.
Figure 19:
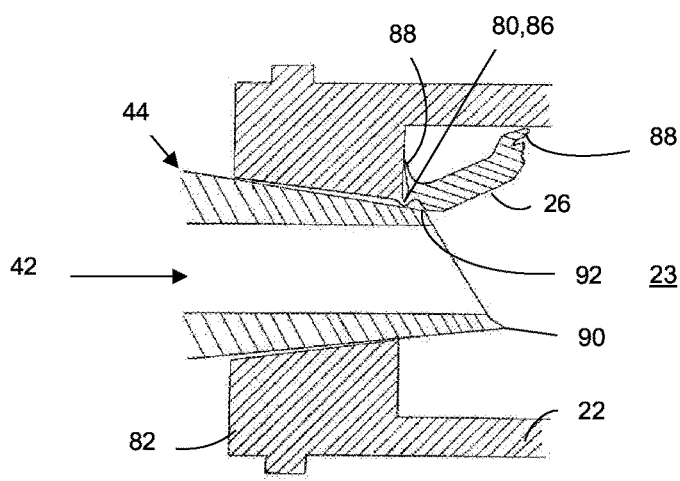
FIG. 19 shows a detail, exploded, cross-sectional view of the piercing head and cartridge end of FIG. 18, after the piercing head has ruptured the septum.
Figure 20:
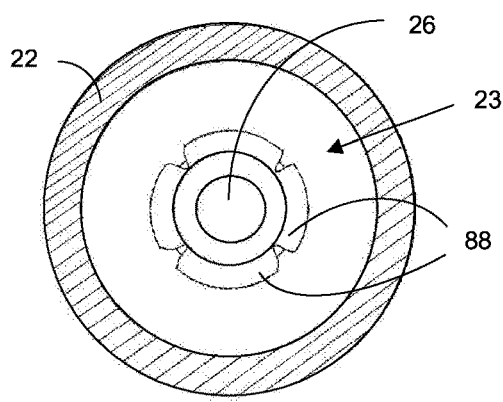
FIG. 20 shows a longitudinal, sectional view of the cartridge end of FIG. 18, taken at XX-XX.

Referring to FIGS. 18 to 20, in a sixth embodiment of the present invention, the septum 26 is substantially rigid and is surrounded along at least part of its periphery by a thin-walled border 80 by which the septum is attached to the closed end of the cartridge 14. The end of the cartridge 14 is a more substantial body 82 in this embodiment, than the disc 24 described in preceding embodiments. The body 82, border 80 and septum 26 are preferably a unitary moulding of the same material, but the body and septum are substantially rigid due to their thickness, whereas the border is thin and flexible.

The border 80 preferably extends contiguously around the septum 26. In particular, the border preferably extends continuously around the septum, but it can extend intermittently around the septum in some embodiments. In some embodiments, the border 80 can extend only partly around the septum 26, but in the illustrated, breferred embodiment, it extends completely around the septum.

Part of the border 80 forms a rupture formation 84 and can rupture when pierced with a sharp object, because it is so thin, whereas part of the border forms; a hinge formation 86 that can allow the septum to hinge relative to the body 82, e.g. when the septum is attached to the body only by the hinge formation. In some embodiments, the rupture formation 84 and hinge formation 86 can be different in shape and/or configuration and there could be more than one of either of these formations along the periphery of the septum 26, but in the illustrated embodiment, the border 80, rupture formations and hinge formations are identical and effectively, any part of the border can serve as either the hinge formation or the rupture formation, as described below.

Four sealing lips 88 extend from the septum 26, on the side of the septum that faces towards the cavity 23. These sealing lips 88 are spaced intermittently along the periphery of the septum 26 and each sealing lip overlaps the border 80—preferably only in part.

The piercing head 44 has a slanted free end, so that it defines a sharp leading edge 90 at its tip and a diametrically opposed, obtuse trailing edge 92. When the cartridge 14 moves towards the piercing head 44 as described above, the leading edge 90 pierces and ruptures a part of the border 80 that forms the rupture formation 84. As the piercing head 44 advances further inwards, towards the cavity 23, the border 80 is ruptured further along the periphery of the septum 26, but a part of the border is impinged by the trailing edge 92, which does not rupture the border. Instead, the remaining un-ruptured part of the border 80 forms the hinge formation 86 and the septum 26, which has been severed from the body 82 along all of its periphery, apart from the hinge formation, hinges on the hinge formation to an open position, out of the way of the piercing head 44, as shown in FIG. 19.

Once the septum 26 has been hinged its open position shown in FIG. 19, the liquid medicine can be expelled from the cavity 23 via the discharge passage 42.

When the cartridge 14 is removed from the dispenser and the piercing head 44 is withdrawn from the cartridge, the resilience of the hinge formation 86 causes the septum 26 to pivot back to towards its initial, closed position. Depending on material selection and detail design, the septum 26 may hinge only part of the way towards its closed position, but it remains attached to the body 82 via the flexible hinge formation 86 and can act as one-way valve.

If pressure is applied to the shell 22 of the cartridge 14, after the rupture formation 84 has been ruptured by the piercing head 44, the pressure could cause the shell to flex inwards and could hold a risk that liquid medicine may be expelled from the cartridge. However, if liquid medicine inside the cavity 23 is placed under pressure, the pressure will urge the septum 26 to hinge or pivot about the hinge formation 86 towards it closed position and to close the opening formed when the piercing head 44 ruptured the rupture formation 84. The septum 26 would not necessarily seal the opening tightly and a small volume of liquid medicine may be expelled before the septum 26 is hinged into the closed position, but the flow of medicine from the cavity 23 will still be substantially reduced or stopped.

Preventing liquid medicine from being expelled from the cartridge 14 reduces the risks of accidental ingestion of the medicine directly from the cartridge and reduces the risk of spillage.

The operation of the septum 26 as a one-way valve, is enhanced by the sealing lips 88, although the sealing lips can be omitted in some embodiments. The sealing lip or lips 88 that extend adjacent the rupture formation 84 improves the seal between the septum 26 and the body 82 by overlapping with the severed rupture formation. The sealing lip or lips 88 that extend adjacent the hinge formation 86 is flexed as the septum 26 is hinged to its open position and resilience of the sealing lip urges the septum to return to its closed position. The discontinuity of the sealing lips 88 along the periphery of the septum 26, as shown in FIG. 20, allows the sealing lips to flex simultaneously, when withdrawing a moulding tool after the cartridge 14 has been moulded.

Referring to all the drawings, the dispenser (comprising the barrel 16, plunger 18 and receiver 20) is made entirely from recyclable plastics and if necessary, different moulding techniques or materials can be used to achieve material properties required for different components. The dispenser can be a single use or multiple use disposable device, can be made inexpensively and can be recycled easily.

In the illustrated embodiments of the invention, the dispenser is configured to receive a single cartridge 14 or four cartridges, but other embodiments can make provision for receiving and dispensing from two or any other number of cartridges, simultaneously.

The invention claimed is:

1. A system for dispensing liquid medicine for oral administration, said system comprising:
   at least one cartridge that includes;
      a hollow, elongate shell that has a longitudinal axis and that defines an internal cavity and that is closed at one end with a substantially rigid septum, at least a first part of the periphery of the septum being attached to the closed end of the shell by at least one rupture formation that is thinner than the septum and is thin enough to rupture when pierced with a sharp object, and at least a second part of the periphery of the septum being attached to the closed end of the shell by at least one hinge formation that is thinner than the septum and is thin enough to allow the septum to hinge relative to the shell, about the hinge formation;
      a piston that is disposed inside the shell and that can slide axially inside the cavity while sealing against the inside of the shell; and
      said liquid medicine being held inside the cavity between the closed end and the piston; and
   a dispenser that includes:
      a body defining a receiving formation in which at least the closed end of the shell of the cartridge is receivable;
      a sharp protuberance disposed in the receiving formation and configured to rupture the rupture formation if the cartridge is moved far enough in the axial direction; and
      a plunger that is displaceable in the axial direction towards the protuberance;
   wherein the system includes at least one sealing lip that extends from the septum, on the side of the septum that faces towards the cavity, said sealing lip overlapping the rupture formation at least in part.

2. The system according to claim 1, wherein the at least one rupture formation and the at least one hinge formation, extend contiguously around the periphery of the septum.

3. The system according to claim 2, wherein the at least one rupture formation and the at least one hinge formation extend continuously along the periphery of the septum to form a continuous thin-walled border along at least part of the periphery of the septum.

4. The system according to claim 3, wherein said thin-walled border extends continuously along the entire periphery of the septum.

5. The system according to claim 1, wherein the at least one rupture formation and the at least one hinge formation extend continuously along the periphery of the septum to form a continuous thin-walled border along at least part of the periphery of the septum.

6. The system according to claim 5, wherein said thin-walled border extends continuously along the entire periphery of the septum.

7. The system according to claim 1, which includes a plurality of said sealing lips that extend contiguously along the periphery of the septum.

8. The system according to claim 7, wherein the dispenser includes a receiver defining a recess in which the cartridge is receivable, at least in part, said plunger being attachable to the receiver, to slide relative to the receiver and cartridge shell in the axial direction.

9. The system according to claim 8, wherein the receiver includes a first detent that is biased towards a locked position in which it prevents sliding movement between the plunger and the receiver, said first detent being displaceable against its bias, by the body, when the receiver engages the body.

10. The system according to claim 9, wherein the receiver includes a second detent that is biased towards a locked position in which it prevents sliding movement between the plunger and the receiver, said second detent being displaceable against its bias, by the cartridge, when the cartridge is received inside the first recess of the receiver.

11. The system according to claim 8, wherein the body defines a stop formation adjacent the sharp protuberance to inhibit the receiver and cartridge from sliding in the axial direction to a point at which the sharp protuberance can rupture the septum, unless the receiver and cartridge are inserted into the body with a correct orientation.

12. The system according to claim 11, wherein a second recess is defined in the receiver, said second recess corresponding to the stop formation and said second recess being configured to receive the stop formation with interference, such that the receiver and cartridge can slide in the axial direction against said interference, while the sharp protuberance ruptures the septum.

13. A cartridge for dispensing liquid medicine for oral administration, said cartridge comprising:
 a hollow, elongate shell that has a longitudinal axis and that defines an internal cavity and that is closed at one end with a substantially rigid septum;
 a piston that is disposed inside the shell and that can slide axially inside the cavity, while sealing against the inside of shell; and
 said liquid medicine being held inside the cavity between the closed end and the piston;
 wherein at least a first part of the periphery of the septum is attached to the closed end of the shell by at least one rupture formation that is thinner than the septum and is thin enough to rupture when pierced with a sharp object;
 wherein at least a second part of the periphery of the septum is attached to the closed end of the shell by at least one hinge formation that is thinner than the septum and is thin enough to allow the septum to hinge relative to the shell, about the hinge formation; and
 wherein the cartridge includes at least one sealing lip that extends from the septum, on the side of the septum that faces towards the cavity, said sealing lip overlapping the rupture formation at least in part.

14. The cartridge according to claim 13, wherein the at least one rupture formation and the at least one hinge formation, extend contiguously around the periphery of the septum.

15. The cartridge according to claim 14, wherein the at least one rupture formation and the at least one hinge formation extend continuously along the periphery of the septum to form a continuous thin-walled border along at least part of the periphery of the septum.

16. The cartridge according to claim 15, wherein said thin-walled border extends continuously along the entire periphery of the septum.

17. The cartridge according to claim 13, wherein the at least one rupture formation and the at least one hinge formation extend continuously along the periphery of the septum to form a continuous thin-walled border along at least part of the periphery of the septum.

18. The cartridge according to claim 17, wherein said thin-walled border extends continuously along the entire periphery of the septum.

19. The cartridge according to claim 13, which includes a plurality of said sealing lips that extend contiguously along the periphery of the septum.

\* \* \* \* \*